United States Patent [19]

Pelosi, Jr.

[11] 4,111,964

[45] Sep. 5, 1978

[54] 3-[5-(4-NITROPHENYL)FUR-FURYLAMINO)]-1,2-PROPANEDIOL HYDROCHLORIDE

[75] Inventor: Stanford S. Pelosi, Jr., Norwich, N.Y.

[73] Assignee: Morton-Norwich Products, Inc., Norwich, N.Y.

[21] Appl. No.: 837,029

[22] Filed: Sep. 27, 1977

[51] Int. Cl.$^2$ .................................... C07D 307/70
[52] U.S. Cl. ................................ 260/347.7; 424/285
[58] Field of Search .................................... 260/347.7

[56] References Cited

U.S. PATENT DOCUMENTS 3,377,359  4/1968  Boissier et al. .............. 260/347.7 X

OTHER PUBLICATIONS

Oleinik et al., Chemical Abstracts, vol. 78 (1973), 43169q.

Primary Examiner—Richard L. Raymond
Attorney, Agent, or Firm—Anthony J. Franze

[57] ABSTRACT

3-[5-(4-Nitrophenyl)furfurylamino]-1,2-propanediol hydrochloride is an effective skeletal muscle relaxant.

1 Claim, No Drawings

3-[5-(4-NITROPHENYL)FURFURYLAMINO)]-1,2-PROPANEDIOL HYDROCHLORIDE

This invention relates to the compound 3-[5-(4-nitrophenyl)furfurylamino]-1,2-propanediol hydrochloride.

This compound possesses pharmacologic activity. In particular, it exhibits skeletal muscle relaxant activity when administered perorally to warm-blooded animals. Thus, when administered perorally as a suspension in a pharmaceutically acceptable vehicle, such as aqueous methyl cellulose, at a dose of 200–800 mg/kg to mice, skeletal muscle relaxant activity is elicited.

The compound of this invention is preferably prepared in accordance with the following example:

A mixture of 43 g (0.20 mole) of 5-(4-nitrophenyl)-2-furancarboxaldehyde and 18 g (0.20 mole) of 3-amino-1,2-propanediol in 600 ml of MeOH was heated under reflux for 2 hrs. and cooled to 15°. Sodium borohydride (6.0 g, 0.16 mole) was added in portions over 1 hr. at 15°–20°. The resulting solution was stirred at ambient temperature for 2 hrs. and allowed to stand overnight. The solution was concentrated on a rotary evaporator to ca. 350 ml and poured into 5 liters of cold water. The solid which was deposited was collected by filtration to give 39 g (67%) of the free base of product. The free base was dissolved in 1400 ml of anhydrous MeOH and treated with HCl gas. The solvent was removed on a rotary evaporator to give a yellow residual solid which was triturated with anhydrous ether. Recrystallization from 3 liters of a 50—50 mixture of isopropanol and anhydrous ether gave 12 g of 3-[5-(p-nitrophenyl)-furfurylamino]-1,2-propanediol hydrochloride, m.p. 166°–170°. The filtrate was evaporated on a rotary evaporator. The residual solid was dissolved in 1 liter of absolute EtOH and treated with 100 ml of ethanolic HCl. The solution was diluted to 2 liters with ethyl acetate and cooled overnight. The solid which was deposited was collected by filtration to give an additional 10 g of product; total yield was 22 g (33%).

Anal. Calcd. For $C_{14}H_{16}N_2O_5 \cdot HCl$: C, 51.15; H, 5.21; N, 8.52. Found: C, 50.89; H, 5.18; N, 8.38.

What is claimed is:

1. The compound 3-[5-(4-nitrophenyl)furfurylamino]-1,2-propanediol hydrochloride.

* * * * *